(12) United States Patent
Leutner et al.

(10) Patent No.: US 6,290,925 B1
(45) Date of Patent: Sep. 18, 2001

(54) FLOWABLE CYANURIC CHLORIDE, PROCESS FOR THE PRODUCTION THEREOF AND USE THEREOF

(75) Inventors: Josef Leutner, Grossheubach; Manfred Schmidt, Gelnhausen, both of (DE)

(73) Assignee: Degussa AG, Frankfurt am Main (DE)

(*) Notice: Subject to any disclaimer, the term of this patent is extended or adjusted under 35 U.S.C. 154(b) by 0 days.

(21) Appl. No.: 09/524,906

(22) Filed: Mar. 13, 2000

(30) Foreign Application Priority Data

Mar. 31, 1999 (DE) .............................. 199 14 616

(51) Int. Cl.⁷ ....................................... C01C 3/08
(52) U.S. Cl. ..................... 423/371; 423/275; 423/383
(58) Field of Search ................................. 423/267, 275, 423/371, 383

(56) References Cited

U.S. PATENT DOCUMENTS

| 4,268,408 | * | 5/1981 | Raspet ................................... 252/182 |
| 4,329,325 | | 5/1982 | Vollbrecht ........................... 423/267 |

FOREIGN PATENT DOCUMENTS

| 1 134 999 | 8/1962 | (DE) . |
| 28 39 384 B1 | 9/1978 | (DE) . |
| 0 416 584 A1 | 3/1991 | (EP) . |

\* cited by examiner

*Primary Examiner*—Steven P. Griffin
*Assistant Examiner*—Maribel Medina
(74) *Attorney, Agent, or Firm*—Pillsbury Winthrop LLP

(57) ABSTRACT

Flowable cyanuric chloride containing hydrophilic silica as a flow auxiliary, the hydrophilic silica is a precipitated silica or silica gel having an average agglomerate diameter of less than 15 $\mu$m. Preferred products exhibit improved bulk density, reactivity and/or flowability properties.

10 Claims, No Drawings

FLOWABLE CYANURIC CHLORIDE, PROCESS FOR THE PRODUCTION THEREOF AND USE THEREOF

CROSS-REFERENCE TO RELATED APPLICATION

This application is based on German Application DE 199 14 616.0, filed Mar. 31, 1999, which disclosure is incorporated herein by reference.

FIELD OF THE INVENTION

This invention relates to flowable cyanuric chloride which contains a hydrophilic silica as flow auxiliary, which cyanuric chloride exhibits an improved range of properties in comparison with prior art cyanuric chloride containing a pyrogenic silica. This invention furthermore relates to a process for the production of the improved flowable cyanuric chloride and to the use thereof.

BACKGROUND OF THE INVENTION

It is known that solid cyanuric chloride readily agglomerates when in finely divided form. In order to eliminate the consequent problems during storage and further processing, DE-AS 11 34 999 teaches the addition of flow auxiliaries to the finely divided cyanuric chloride, selected from the range of finely divided silicon dioxide, titanium dioxide, aluminium oxide, aluminium silicate and calcium silicate, in a quantity of 0.3 to 3 wt. %. Only one pyrogenically produced silica, namely AEROSIL® (Degussa-Hüls AG, Germany) is mentioned among the silicas stated in this document as flow auxiliaries. No suggestion is made to use silicas of other origins.

As is disclosed by DE-AS 28 39 384, using a hydrophobic pyrogenic or hydrophobic precipitated silica makes it possible not only to improve the flowability of cyanuric chloride, but also to counteract the unwanted hydrolysis of cyanuric chloride which occurs during storage and in-plant handling. Hydrolysis products formed during the storage and conversion of cyanuric chloride reduce the quality and/or yield of the reaction products.

In the process according to EP-A 0 416 584, an attempt was made to improve the flowability of solid cyanuric chloride by subjecting the cyanuric chloride to shear forces in a kneader or mixer while heating it to a temperature below the melting point. However, it was found (see Comparative Examples) that the reactivity of such products is reduced. Due to the inadequate storage stability of products treated in this manner, this process has not become established in practice, such that most commercial products still contain a hydrophilic pyrogenic silica or a hydrophobic pyrogenic or precipitated silica as a flow auxiliary.

A substantial disadvantage not only of all hydrophilic pyrogenic silicas as well as hydrophobic pyrogenic silicas but also of hydrophobic precipitated silicas is the high cost thereof, due to the production process. Specialist manufacturers are accordingly interested in lower cost alternatives, wherein these alternatives must exhibit an at least equivalent range of properties.

SUMMARY OF THE INVENTION

The object of the present invention is accordingly to provide a cyanuric chloride obtainable in an economic manner having a range of properties at least equal to that of current commercial products, but preferably surpassing current products in one respect or another. The range of properties substantially includes:

(i) a maximally high bulk density
(ii) good flowability corresponding to a rating of less than or equal to 3, preferably less than or equal to 2, and
(iii) maximally high reactivity, wherein this property should, where possible, not be impaired in comparison with untreated cyanuric chloride, but should preferably even be improved.

This object is achieved by a flowable cyanuric chloride having a flowability rating of less than or equal to 3, containing a hydrophilic silica as flow auxiliary, which cyanuric chloride is characterized in that the hydrophilic silica is a precipitated silica or silica gel having an average agglomerate diameter of less than or equal to 15 μm, determined using a Coulter Counter. Precipitated silicas are preferred as the flow auxiliary.

Preferred products have an average agglomerate diameter of less than 7 μm, preferably of less than 5 μm. It has furthermore been established that in particular hydrophilic precipitated silicas exhibiting DBP absorption of below 270 g/100 g provide a particularly good range of properties of the flowable cyanuric chloride. Precipitated silicas and silica gels exhibit various structures as a result of the production method used. The flow auxiliaries preferably comprise ground precipitated silicas, in particular steam or air jet ground precipitated silicas having an agglomerate diameter of less than 5 μm and DBP absorption in the range from 200 to 260 g/100 g. The precipitated silicas and silica gels in question conventionally comprise products having a BET surface area of at least 100 $m^2/g$; products having a BET surface area in the range from 100 to 500 $m^2/g$, are preferably used and a BET surface area from 150 to 300 $m^2/g$, is particularly preferably used.

One particularly important criterion of the range of properties of the flowable cyanuric chloride is the bulk density achieved when using the flow auxiliary and under defined mixing conditions. It is of particular interest to achieve a maximally high bulk density with regard to the packaging volume of the flowable cyanuric chloride. Absolute bulk density is dependent not only upon the flow auxiliary content and mixing conditions, but also, as may be understood, upon the grain size distribution of the cyanuric chloride used. It has been found that a higher bulk density may be achieved when using flow auxiliaries according to the invention than when using a hydrophilic pyrogenic silica such as AEROSIL® 200. At an identical usage rate and under identical mixing conditions, the bulk density of a preferred flowable cyanuric chloride is comparable with that which is achieved using a hydrophobic precipitated silica, but surprisingly is higher than that obtainable using a hydrophilic pyrogenic silica.

Another criterion of the range of properties is flowability: the ratings are obtained from the results of using standardized flow funnels having outlet diameters in the range between 2.5 and 18 mm. A product which flows without stoppage from a 25 funnel having an outlet diameter of 8 mm or 5 mm receives a rating of 3 or 2, respectively. Products having a rating of 2 or less than 2 are preferred. Precipitated silicas and silica gels having an agglomerate diameter of greater than 15 μm do not yield any satisfactory flowability ratings.

The reactivity of the flowable cyanuric chloride constitutes the third criterion of the required range of properties. Reactivity is determined by hydrolyzing cyanuric chloride in an aqueous medium under defined conditions and measuring the time taken to reach a pH value of 7. A maximally high reactivity is desired, i.e. a short time until a pH value of 7 is achieved. While reactivity is distinctly reduced in comparison with untreated cyanuric chloride when hydrophobic precipitated or pyrogenic silica is used, the reactivity of flowable cyanuric chloride according to the invention substantially matches that of untreated cyanuric chloride and the reactivity of products according to the invention preferably exceeds that of the untreated cyanuric chloride. The reactivity of products according to the invention is within the range of that which is obtainable using a hydrophilic pyrogenic silica, but preferred products have a still higher reactivity.

One unexpected advantage of products according to the invention is that these products exhibit an extraordinarily low hydrolyzate content. The hydrolyzate content comprises toluene-insoluble products which are formed by hydrolysis of the cyanuric chloride. The hydrolyzate content is determined after a specified period of storage after production of the flowable cyanuric chloride. It has been found that the hydrolyzate content found when using the preferred precipitated silicas and silica gels is surprisingly substantially lower than that obtained when using hydrophobic silicas. This is surprising because hydrophobic silicas have hitherto been used specifically to provide an effective shell around the cyanuric chloride particles which are sensitive to hydrolysis and so to hinder hydrolysis.

The precipitated silicas or silica gels to be used according to the invention comprise products which, as a result of the production thereof, are obtainable at a lower cost than pyrogenically produced or/and hydrophobic silicas. The elevated reactivity and elevated bulk density of the products constitute further advantages. One additional advantage of products according to the invention is that, when packages are emptied, the product does not become statically charged and thus does not adhere to the packaging material.

The quantity of flow auxiliary used is in the range from 0.05 to 5 wt. %, preferably from 0.05 to 0.5 wt. % and in particular from 0.1 to 0.3 wt. %.

The products according to the invention are produced in a manner known per se by homogeneously mixing the cyanuric chloride powder with the flow auxiliary. Conventional mixing apparatus is used for this purpose. While bulk density may indeed be increased by extending the duration of mixing, the above-stated difference between the hydrophilic silicas to be used according to the invention and a pyrogenic hydrophilic silica still subsists. The flow auxiliary may be incorporated immediately after production of the pulverulent cyanuric chloride or may be achieved by a separate mixing process.

Since elevated reactivity of the flowable cyanuric chloride is maintained, it may be used to produce cyanuric chloride derivatives in which one, two or three chlorine atoms of the cyanuric chloride are substituted. In such cases, the elevated reactivity and low hydrolyzate content give rise to short reaction times and pure products.

The invention is illustrated by means of the following Examples and Comparative Examples; the test methods are also described.

DETAILED DESCRIPTION OF THE PREFERRED EMBODIMENTS

Determination of Bulk Density (BD)

A 100 ml measuring cylinder, cut off at exactly 100 ml, is filled with product by of a funnel and the protruding cone of material is scraped off. Any adhering to the outside of the measuring cylinder is cleaned off and the cylinder is then weighed. Value in g/l.

Determination of Flowability (F)

The sample to be tested is introduced into a cylindrical flow vessel, the lower portion of which is funnel shaped, while the outlet orifice is kept closed. If the outlet orifice is opened, the product flows out without stoppage. If necessary, outflow may be started by knocking the vessel with a spatula. There are 5 flow vessels with different sizes of outlet orifices.

Vessesls: height=90 mm, internal diameter=42 mm

| Vessel no. | Outlet orifice diameter (mm) |
|---|---|
| 1 | 2.5 |
| 2 | 5 |
| 3 | 8 |
| 4 | 12 |
| 5 | 18 |

Rating:
1 = flows smoothly through vessel 1 (smallest orifice)
5 = flows through vessel 5 (largest orifice)
6 = does not flow through vessel 5

Determination of Reactivity (R)

Cyanuric chloride undergoes hydrolysis in an aqueous solution. Cyanuric chloride hydrolyzes to form cyanuric acid. This reaction, which proceeds with a falling pH value more or less rapidly depending upon the reactivity, is used when determining the reactivity of cyanuric chloride. The decrease in pH value may be monitored by means of a pH meter. The time (min.) taken to reach a pH of 7 is used as a measure of reactivity.

Precisely 9.22 g of cyanuric chloride (0.05 mol) of the sample are weighed out into a 150 ml beaker, a stir bar is introduced and the beaker placed on a magnetic stirrer. Precisely 100 ml of 1N NaOH (0.1 mol) are added by pipette. As soon as the NaOH is added, the stopwatch and stirrer are started and the mixture stirred vigorously enough to ensure thorough mixing. After exactly 1 minute, the beaker is placed in a water bath adjusted to 30° C. and the pH electrode dipped in. Consumption of the NaOH is monitored while the mixture is vigorously stirred (the cyanuric chloride must be swirled in the solution). The endpoint of the determination is reached at a pH of 7 and the timer is stopped.

Determination of Hydrolyzate Content

Using a precision balance, approx. 5 g of cyanuric chloride are weighed out to an accuracy of 0.1 g into a ground joint conical flask and combined with approx. 100 ml of toluene. Once the conical flask has been sealed, dissolution of the cyanuric chloride is accelerated by shaking. If no turbidity is visible once the cyanuric chloride has completely dissolved, the hydrolyzate content is <0.1% and the determination may be terminated. In the event of turbidity or formation of a precipitate, the solution is filtered through a desiccated and tared glass filter crucible and then washed with 20 ml of toluene. The filter crucible should be dried to constant weight in a drying cabinet at approx. 120° C. The final weight corresponds to the sum of hydrolyzate and flow auxiliary. The proportion of flow auxiliary may be determined by leaching the precipitate with hot water and drying the residue.

EXAMPLES B1 TO B3 AND COMPATATINE EXAMPLES VB1 TO VB3

A flowable cyanuric chloride was produced by mixing finely divided cyanuric chloride (batch 391) with 0.3 wt. % of the stated silica (S) for 15 minutes in a container on a roller unit with the container rolling slowly. Table 1 shows the results for bulk density (BD), reactivity (R) and flowability (F).

TABLE 1

| No. | Silica*) (grade) | BD (g/l) | R (min.) | F |
|---|---|---|---|---|
| VB1 | — | 655 | 7.5 | 4–5 |
| VB2 | AEROSIL 200 hydrophilic, pyrogenic | 746 | 8.5 | 2 |
| VB3 | AEROSIL R812 hydrophobic, pyrogenic | 764 | 18.5 | 2 |
| B1 | FK 320 DS hydrophilic, pyrogenic; $d_{50} = 4$ μm DBP absorption 230 g/100 g | 778 | 6.8 | 1 |
| B2 | SIPERNAT 50 S hydrophilic, precipitated, DBP absorption 330 g/100 g | 790 | 7.5 | 3–4**) |
| B3 | FK 50 LS hydrophilic, precipitated; $d_{50}$ 3.5 μm DBP absorption 330 g/100 g | 755 | 6.8 | 3**) |

*) The products used are silicas of Degussa-Huls AG. The silicas of Examples B1 to B3 are ground products.
**) F values of less than 3 are achieved with a somewhat higher content of flow auxiliary or a blend of SIPERNAT 50 S or FK 500 LS with, for example, FK 320 DS.

EXAMPLES B4 AND B5 AND COMPARATIVE EXAMPLE VB4 TO VB6

Cyanuric chloride (CC) (batch 391) and a still more finely divided batch (batch 399) were rendered flowable by using 0.25 wt. % of AEROSILO® silica or FK 320 DS silica. The results are shown in the table. Mean from 5 determinations.

TABLE 2

| No. | CC* (grade) | Silica (grade) | BD (g/l) | R (min.) | F |
|---|---|---|---|---|---|
| VB1 | 391 | — | 655 | 7.5 | 4–5 |
| VB4 | 391 | AEROSIL® 200 | 733 | 7.9 | 2 |
| B4 | 391 | FK 320 DS | 773 | 7.0 | 2 |
| VB5 | 399 | — | 636 | 7.6 | 4–5 |
| VB6 | 399 | AEROSIL® 200 | 795 | 6.8 | 2 |
| B5 | 399 | FK 320 DS | 830 | 6.8 | 1–2 |

EXAMPLE B6 AND COMPARATIVE EXAMPLES VB7 TO VB6

A flowable cyanuric chloride was produced, wherein the cyanuric chloride used was less finely divided than batches 391 and 399. The content of flow auxiliary was 0.3 wt. %. Mixing was performed for 15 minutes in a mixing vessel rotating on a roller unit. The results are shown in Table 3. Mean values each from 10 determinations and the standard deviation s in % are stated for bulk density, reactivity, hydrolyzate content and flowability values.

TABLE 3

| No. | Silica (grade) | BD (g/l) (s %) | R (min.) (s %) | F | Hydrolyzate (%) (s %) |
|---|---|---|---|---|---|
| VB7 | — | 731 | 12.1 | 4–5 | <0.05 |
| B4 | FK 320 DS precipitated; hydrophilic | 866 (0.7) | 10.9 (8) | 1 | 0.33 (1.6) |
| VB8 | AEROSIL® R974 hydrophobic | 844 (0.6) | 14.8 (7.2) | 1–2 | 0.47 (4.8) |

The Examples demonstrate the outstanding combination of properties in comparison with that of the Comparative Examples.

What is claimed is:

1. Flowable cyanuric chloride having a flowability rating of less than or equal to 3 containing a hydrophilic silica as a flow auxiliary, wherein the hydrophilic silica is a precipitated silica or silica gel having an average agglomerate diameter of less than 15 μm, determined using a Coulter Counter.

2. Flowable cyanuric chloride according to claim 1, wherein the hydrophilic silica exhibits a DBP absorption of less than 270 g/100 g.

3. Flowable cyanuric chloride according to claim 1, wherein the hydrophilic silica is ground and exhibits an average agglomerate diameter of less than 7 μm.

4. Flowable cyanuric chloride according to claim 1, wherein the flow auxiliary comprises a steam or air jet ground precipitated silica having an average agglomerate diameter of less than or equal to 5 μm.

5. Flowable cyanuric chloride according to claim 2, wherein the hydrophilic silica is a precipitated silica and exhibits a DBP absorption value to DIN 53601 of less than 270 g/100 g.

6. Flowable cyanuric chloride according to claim 1, wherein the precipitated silica exhibits a BET surface area of 100 to 500 m²/g.

7. Flowable cyanuric chloride according to claim 6, wherein the precipitated silica exhibits a BET surface area of 150 to 300 m²/g.

8. Flowable cyanuric chloride according to claim 1, comprising at least one member selected from the group consisting of precipitated silicas and silica gels having an average agglomerate diameter of less than or equal to 15 μm in a total quantity of 0.05 to 0.5 wt. %.

9. A process for the production of a flowable cyanuric chloride according to claim 1, comprising homogeneously mixing cyanuric chloride and at least one member selected from the group consisting of precipitated silicas and silica gels having an agglomerate diameter of less than 15 μm.

10. A method for the production of cyanuric chloride derivatives in which one, two or three chlorine atoms of the cyanuric chloride are substituted, comprising substituting at least one of the chlorine atoms in a flowable cyanuric chloride according to claim 1, to form an organic chloride derivative.

* * * * *